United States Patent
Olson et al.

(10) Patent No.: US 8,453,909 B2
(45) Date of Patent: *Jun. 4, 2013

(54) CENTER CINCH AND RELEASE OF BUTTRESS MATERIAL

(75) Inventors: Lee Olson, Wallingford, CT (US); Ernie Aranyi, Easton, CT (US); Patrick Mozdzierz, Rocky Hill, CT (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/545,031

(22) Filed: Jul. 10, 2012

(65) Prior Publication Data

US 2012/0273552 A1 Nov. 1, 2012

Related U.S. Application Data

(63) Continuation of application No. 13/111,050, filed on May 19, 2011, now Pat. No. 8,235,273, which is a continuation of application No. 12/414,961, filed on Mar. 31, 2009, now Pat. No. 7,967,179.

(51) Int. Cl.
*A61B 17/068* (2006.01)
*A61B 17/064* (2006.01)

(52) U.S. Cl.
USPC ............... 227/176.1; 227/175.1; 227/181.1; 227/180.1; 606/151; 606/219; 606/139

(58) Field of Classification Search
USPC ...... 227/175.1, 176.1, 181.1, 180.1; 606/151, 606/219, 139
See application file for complete search history.

(56) References Cited

U.S. PATENT DOCUMENTS

| 3,054,406 | A | 9/1962 | Usher |
| 3,124,136 | A | 3/1964 | Usher |
| 4,347,847 | A | 9/1982 | Usher |
| 4,354,628 | A | 10/1982 | Green |
| 4,452,245 | A | 6/1984 | Usher |
| 4,605,730 | A | 8/1986 | Shalaby et al. |
| 4,655,221 | A | 4/1987 | Devereux |
| 4,834,090 | A | 5/1989 | Moore |
| 4,838,884 | A | 6/1989 | Dumican et al. |

(Continued)

FOREIGN PATENT DOCUMENTS

| DE | 199 24 311 | 11/2000 |
| DE | 199 24 311 A1 | 11/2000 |

(Continued)

OTHER PUBLICATIONS

International Search Report corresponding to European Application No. EP 12 15 2229.6, completed on Feb. 23, 2012 and mailed on Mar. 1, 2012; 4 pages.

(Continued)

*Primary Examiner* — M. Alexandra Elve
*Assistant Examiner* — Michelle Lopez

(57) ABSTRACT

A buttressed anvil assembly is provided for use with a surgical stapling instrument. The buttressed anvil assembly generally includes an anvil member having a strip of buttress material attached thereto by a pair of sutures. A tensioning mechanism is provided to secure or tension the buttress material to the anvil member prior to use and allow for release of the buttress material after stapling of tissue. The tensioning mechanism includes a cinch track engageable with one of the pair of sutures.

16 Claims, 5 Drawing Sheets

U.S. PATENT DOCUMENTS

| | | | |
|---|---|---|---|
| 4,925,082 A | 5/1990 | Kim | |
| 4,930,674 A | 6/1990 | Barak | |
| 5,002,551 A | 3/1991 | Linsky et al. | |
| 5,014,899 A | 5/1991 | Presty et al. | |
| 5,040,715 A | 8/1991 | Green et al. | |
| 5,065,929 A | 11/1991 | Schulze et al. | |
| 5,205,459 A | 4/1993 | Brinkerhoff et al. | |
| 5,263,629 A | 11/1993 | Trumbull et al. | |
| 5,314,471 A | 5/1994 | Brauker et al. | |
| 5,344,454 A | 9/1994 | Clarke et al. | |
| 5,392,979 A | 2/1995 | Green et al. | |
| 5,397,324 A | 3/1995 | Carroll et al. | |
| 5,425,745 A | 6/1995 | Green et al. | |
| 5,441,193 A | 8/1995 | Gravener | |
| 5,441,507 A | 8/1995 | Wilk et al. | |
| 5,468,253 A | 11/1995 | Bezwada et al. | |
| 5,503,638 A | 4/1996 | Cooper et al. | |
| 5,542,594 A | 8/1996 | McKean et al. | |
| 5,549,628 A | 8/1996 | Cooper et al. | |
| 5,575,803 A | 11/1996 | Cooper et al. | |
| 5,653,756 A | 8/1997 | Clarke et al. | |
| 5,683,809 A | 11/1997 | Freeman et al. | |
| 5,690,675 A | 11/1997 | Sawyer et al. | |
| 5,702,409 A | 12/1997 | Rayburn et al. | |
| 5,752,965 A | 5/1998 | Francis et al. | |
| 5,762,256 A | 6/1998 | Mastri et al. | |
| 5,766,188 A | 6/1998 | Igaki | |
| 5,769,892 A | 6/1998 | Kingwell | |
| 5,782,396 A | 7/1998 | Mastri et al. | |
| 5,799,857 A | 9/1998 | Robertson et al. | |
| 5,810,855 A | 9/1998 | Rayburn et al. | |
| 5,814,057 A | 9/1998 | Oi et al. | |
| 5,833,695 A | 11/1998 | Yoon | |
| 5,843,096 A | 12/1998 | Igaki et al. | |
| 5,895,412 A | 4/1999 | Tucker | |
| 5,902,312 A | 5/1999 | Frater et al. | |
| 5,908,427 A | 6/1999 | McKean et al. | |
| 5,915,616 A | 6/1999 | Viola et al. | |
| 5,931,847 A | 8/1999 | Bittner et al. | |
| 5,964,774 A | 10/1999 | McKean et al. | |
| 5,997,895 A | 12/1999 | Narotam et al. | |
| 6,019,791 A | 2/2000 | Wood | |
| 6,030,392 A | 2/2000 | Dakov | |
| 6,032,849 A | 3/2000 | Mastri et al. | |
| 6,045,560 A | 4/2000 | McKean et al. | |
| 6,063,097 A | 5/2000 | Oi et al. | |
| 6,080,169 A | 6/2000 | Turtel | |
| 6,099,551 A | 8/2000 | Gabbay | |
| 6,149,667 A | 11/2000 | Hovland et al. | |
| 6,155,265 A | 12/2000 | Hammerslag | |
| 6,210,439 B1 | 4/2001 | Firmin et al. | |
| 6,214,020 B1 | 4/2001 | Mulhauser et al. | |
| 6,241,139 B1 | 6/2001 | Milliman et al. | |
| 6,258,107 B1 | 7/2001 | Balazs et al. | |
| 6,267,772 B1 | 7/2001 | Mulhauser et al. | |
| 6,273,897 B1 | 8/2001 | Dalessandro et al. | |
| 6,280,453 B1 | 8/2001 | Kugel et al. | |
| 6,299,631 B1 | 10/2001 | Shalaby | |
| 6,312,457 B1 | 11/2001 | DiMatteo et al. | |
| 6,312,474 B1 | 11/2001 | Francis et al. | |
| 6,325,810 B1 | 12/2001 | Hamilton et al. | |
| 6,436,030 B2 | 8/2002 | Rehil | |
| 6,454,780 B1 | 9/2002 | Wallace | |
| 6,461,368 B2 | 10/2002 | Fogarty et al. | |
| 6,503,257 B2 | 1/2003 | Grant et al. | |
| 6,514,283 B2 | 2/2003 | DiMatteo et al. | |
| 6,517,566 B1 | 2/2003 | Hovland et al. | |
| 6,551,356 B2 | 4/2003 | Rousseau | |
| 6,592,597 B2 | 7/2003 | Grant et al. | |
| 6,638,285 B2 | 10/2003 | Gabbay | |
| 6,652,594 B2 | 11/2003 | Francis et al. | |
| 6,656,193 B2 | 12/2003 | Grant et al. | |
| 6,669,735 B1 | 12/2003 | Pelissier | |
| 6,677,258 B2 | 1/2004 | Carroll et al. | |
| 6,685,714 B2 | 2/2004 | Rousseau | |
| 6,704,210 B1 | 3/2004 | Myers | |
| 6,723,114 B2 | 4/2004 | Shalaby | |
| 6,726,706 B2 | 4/2004 | Dominguez | |
| 6,736,823 B2 | 5/2004 | Darois et al. | |
| 6,736,854 B2 | 5/2004 | Vadurro et al. | |
| 6,746,458 B1 | 6/2004 | Cloud | |
| 6,773,458 B1 | 8/2004 | Brauker et al. | |
| 6,927,315 B1 | 8/2005 | Heinecke et al. | |
| 7,128,748 B2 | 10/2006 | Mooradian et al. | |
| 7,147,138 B2* | 12/2006 | Shelton, IV | 227/176.1 |
| 7,434,717 B2 | 10/2008 | Shelton, IV et al. | |
| 7,438,209 B1 | 10/2008 | Hess et al. | |
| 7,547,312 B2 | 6/2009 | Bauman et al. | |
| 7,559,937 B2 | 7/2009 | de la Torre et al. | |
| 7,604,151 B2 | 10/2009 | Hess et al. | |
| 7,665,646 B2 | 2/2010 | Prommersberger | |
| 7,669,747 B2 | 3/2010 | Weisenburgh, II et al. | |
| 7,744,627 B2 | 6/2010 | Orban, III et al. | |
| 7,793,813 B2 | 9/2010 | Bettuchi | |
| 7,823,592 B2 | 11/2010 | Bettuchi et al. | |
| 7,845,533 B2 | 12/2010 | Marczyk et al. | |
| 7,845,536 B2 | 12/2010 | Viola et al. | |
| 7,909,224 B2 | 3/2011 | Prommersberger | |
| 8,235,273 B2* | 8/2012 | Olson et al. | 227/175.1 |
| 2002/0016626 A1 | 2/2002 | DiMatteo et al. | |
| 2002/0019187 A1 | 2/2002 | Carroll et al. | |
| 2002/0028243 A1 | 3/2002 | Masters | |
| 2002/0052622 A1 | 5/2002 | Rousseau | |
| 2002/0091397 A1 | 7/2002 | Chen | |
| 2002/0133236 A1 | 9/2002 | Rousseau | |
| 2002/0138152 A1 | 9/2002 | Francis et al. | |
| 2002/0151911 A1 | 10/2002 | Gabbay | |
| 2002/0165559 A1 | 11/2002 | Grant et al. | |
| 2002/0165562 A1 | 11/2002 | Grant et al. | |
| 2002/0165563 A1 | 11/2002 | Grant et al. | |
| 2002/0177859 A1 | 11/2002 | Monassevitch et al. | |
| 2003/0065345 A1 | 4/2003 | Weadock | |
| 2003/0065346 A1 | 4/2003 | Evens et al. | |
| 2003/0083676 A1 | 5/2003 | Wallace | |
| 2003/0088256 A1 | 5/2003 | Conston et al. | |
| 2003/0105510 A1 | 6/2003 | DiMatteo et al. | |
| 2003/0114866 A1 | 6/2003 | Ulmsten et al. | |
| 2003/0120284 A1 | 6/2003 | Palacios | |
| 2003/0167064 A1 | 9/2003 | Whayne | |
| 2003/0181927 A1 | 9/2003 | Wallace | |
| 2003/0183671 A1 | 10/2003 | Mooradian et al. | |
| 2003/0208231 A1 | 11/2003 | Williamson, IV et al. | |
| 2004/0034377 A1 | 2/2004 | Sharkawy et al. | |
| 2004/0092960 A1 | 5/2004 | Abrams et al. | |
| 2004/0093029 A1 | 5/2004 | Zubik et al. | |
| 2004/0107006 A1 | 6/2004 | Francis et al. | |
| 2004/0116945 A1 | 6/2004 | Sharkawy et al. | |
| 2004/0142621 A1 | 7/2004 | Carroll et al. | |
| 2004/0172048 A1 | 9/2004 | Browning | |
| 2004/0209059 A1 | 10/2004 | Foss | |
| 2004/0215214 A1 | 10/2004 | Crews et al. | |
| 2004/0215219 A1 | 10/2004 | Eldridge et al. | |
| 2004/0215221 A1 | 10/2004 | Suyker et al. | |
| 2004/0254590 A1 | 12/2004 | Hoffman et al. | |
| 2004/0260315 A1 | 12/2004 | Dell et al. | |
| 2005/0002981 A1 | 1/2005 | Lahtinen et al. | |
| 2005/0021026 A1 | 1/2005 | Baily | |
| 2005/0021053 A1 | 1/2005 | Heinrich | |
| 2005/0021085 A1 | 1/2005 | Abrams et al. | |
| 2005/0059996 A1 | 3/2005 | Bauman et al. | |
| 2005/0059997 A1 | 3/2005 | Bauman et al. | |
| 2005/0070929 A1 | 3/2005 | Dalessandro et al. | |
| 2005/0118435 A1 | 6/2005 | DeLucia et al. | |
| 2005/0143756 A1 | 6/2005 | Jankowski | |
| 2005/0149073 A1 | 7/2005 | Arani et al. | |
| 2005/0228446 A1 | 10/2005 | Mooradian et al. | |
| 2005/0245965 A1 | 11/2005 | Orban et al. | |
| 2006/0004407 A1 | 1/2006 | Hiles et al. | |
| 2006/0085034 A1 | 4/2006 | Bettuchi | |
| 2006/0135992 A1 | 6/2006 | Bettuchi et al. | |
| 2006/0173470 A1 | 8/2006 | Oray et al. | |
| 2006/0178683 A1 | 8/2006 | Shimoji et al. | |
| 2006/0212050 A1 | 9/2006 | D'Agostino et al. | |
| 2006/0271104 A1 | 11/2006 | Viola et al. | |
| 2007/0026031 A1 | 2/2007 | Bauman et al. | |
| 2007/0034669 A1 | 2/2007 | de la Torre et al. | |
| 2007/0049953 A2 | 3/2007 | Shimoji et al. | |

| | | | |
|---|---|---|---|
| 2007/0123839 A1 | 5/2007 | Rousseau et al. | |
| 2007/0179528 A1 | 8/2007 | Soltz et al. | |
| 2007/0203509 A1 | 8/2007 | Bettuchi | |
| 2007/0203510 A1 | 8/2007 | Bettuchi | |
| 2007/0246505 A1 | 10/2007 | Pace-Floridia et al. | |
| 2008/0029570 A1 | 2/2008 | Shelton et al. | |
| 2008/0082126 A1 | 4/2008 | Murray et al. | |
| 2008/0110959 A1 | 5/2008 | Orban et al. | |
| 2008/0125812 A1 | 5/2008 | Zubik et al. | |
| 2008/0140115 A1 | 6/2008 | Stopek | |
| 2008/0161831 A1 | 7/2008 | Bauman et al. | |
| 2008/0161832 A1 | 7/2008 | Bauman et al. | |
| 2008/0169327 A1 | 7/2008 | Shelton et al. | |
| 2008/0169328 A1 | 7/2008 | Shelton | |
| 2008/0169329 A1 | 7/2008 | Shelton et al. | |
| 2008/0169330 A1 | 7/2008 | Shelton et al. | |
| 2008/0169331 A1 | 7/2008 | Shelton et al. | |
| 2008/0169332 A1 | 7/2008 | Shelton et al. | |
| 2008/0169333 A1 | 7/2008 | Shelton et al. | |
| 2008/0290134 A1 | 11/2008 | Bettuchi et al. | |
| 2008/0308608 A1 | 12/2008 | Prommersberger | |
| 2008/0314960 A1 | 12/2008 | Marczyk et al. | |
| 2009/0001121 A1 | 1/2009 | Hess et al. | |
| 2009/0001122 A1 | 1/2009 | Prommersberger et al. | |
| 2009/0001123 A1 | 1/2009 | Morgan et al. | |
| 2009/0001124 A1 | 1/2009 | Hess et al. | |
| 2009/0001125 A1 | 1/2009 | Hess et al. | |
| 2009/0001126 A1 | 1/2009 | Hess et al. | |
| 2009/0001128 A1 | 1/2009 | Weisenburgh, II et al. | |
| 2009/0001130 A1 | 1/2009 | Hess et al. | |
| 2009/0005808 A1 | 1/2009 | Hess et al. | |
| 2009/0030452 A1 | 1/2009 | Bauman et al. | |
| 2009/0043334 A1 | 2/2009 | Bauman et al. | |
| 2009/0076510 A1 | 3/2009 | Bell et al. | |
| 2009/0076528 A1 | 3/2009 | Sgro | |
| 2009/0078739 A1 | 3/2009 | Viola | |
| 2009/0095791 A1 | 4/2009 | Eskaros et al. | |
| 2009/0095792 A1 | 4/2009 | Bettuchi | |
| 2009/0120994 A1 | 5/2009 | Murray et al. | |
| 2009/0134200 A1 | 5/2009 | Tarinelli et al. | |
| 2009/0206125 A1 | 8/2009 | Huitema et al. | |
| 2009/0206126 A1 | 8/2009 | Huitema et al. | |
| 2009/0206139 A1 | 8/2009 | Hall et al. | |
| 2009/0206141 A1 | 8/2009 | Huitema et al. | |
| 2009/0206142 A1 | 8/2009 | Huitema et al. | |
| 2009/0206143 A1 | 8/2009 | Huitema et al. | |
| 2009/0218384 A1 | 9/2009 | Aranyi | |
| 2009/0277947 A1 | 11/2009 | Viola | |
| 2009/0287230 A1 | 11/2009 | D'Agostino et al. | |
| 2010/0012704 A1 | 1/2010 | Tarinelli Racenet et al. | |
| 2010/0065606 A1 | 3/2010 | Stopek | |
| 2010/0065607 A1 | 3/2010 | Orban, III et al. | |
| 2010/0072254 A1 | 3/2010 | Aranyi et al. | |
| 2010/0147921 A1 | 6/2010 | Olson | |
| 2010/0147922 A1 | 6/2010 | Olson | |
| 2010/0147923 A1 | 6/2010 | D'Agostino et al. | |
| 2010/0243707 A1 | 9/2010 | Olson et al. | |
| 2010/0243708 A1 | 9/2010 | Aranyi et al. | |
| 2010/0243711 A1 | 9/2010 | Olson et al. | |
| 2010/0249805 A1 | 9/2010 | Olson et al. | |
| 2010/0264195 A1 | 10/2010 | Bettuchi | |
| 2010/0282815 A1 | 11/2010 | Bettuchi et al. | |
| 2011/0024476 A1 | 2/2011 | Bettuchi et al. | |
| 2011/0024481 A1 | 2/2011 | Bettuchi et al. | |
| 2011/0036894 A1 | 2/2011 | Bettuchi | |
| 2011/0042442 A1 | 2/2011 | Viola et al. | |
| 2011/0046650 A1 | 2/2011 | Bettuchi | |
| 2011/0057016 A1 | 3/2011 | Bettuchi | |
| 2011/0087279 A1 | 4/2011 | Shah et al. | |

FOREIGN PATENT DOCUMENTS

| | | |
|---|---|---|
| EP | 0 594 148 | 4/1994 |
| EP | 0 327 022 | 4/1995 |
| EP | 0 667 119 | 8/1995 |
| EP | 1 064 883 | 1/2001 |
| EP | 1 256 317 | 11/2002 |
| EP | 1 520 525 | 4/2005 |
| EP | 1 621 141 | 2/2006 |
| EP | 1 702 570 A1 | 9/2006 |
| EP | 1 759 640 | 3/2007 |
| EP | 1 815 804 A2 | 8/2007 |
| EP | 1 994 890 | 11/2008 |
| EP | 2 005 894 | 12/2008 |
| EP | 2 005 895 | 12/2008 |
| EP | 2 008 595 A2 | 12/2008 |
| EP | 2 198 787 A1 | 6/2010 |
| EP | 2 236 098 A2 | 10/2010 |
| JP | 2000-166933 | 6/2000 |
| JP | 07-124166 | 5/2007 |
| WO | WO 90/05489 | 5/1990 |
| WO | WO 96/22055 | 7/1996 |
| WO | WO 97/01989 | 1/1997 |
| WO | WO 97/13463 | 4/1997 |
| WO | WO 98/17180 | 4/1998 |
| WO | WO 99/45849 | 9/1999 |
| WO | WO 03/082126 | 10/2003 |
| WO | WO 03/105698 | 12/2003 |
| WO | WO 2006/023578 | 3/2006 |
| WO | WO 2006/044490 | 4/2006 |
| WO | WO 2006/083748 | 8/2006 |
| WO | WO 2007/121579 | 11/2007 |
| WO | WO 2008/057281 | 5/2008 |
| WO | WO 2008/109125 | 9/2008 |
| WO | WO 2010/075298 A2 | 7/2010 |
| WO | WO 2011/143183 A2 | 11/2011 |
| WO | WO 2012/044848 A1 | 4/2012 |

OTHER PUBLICATIONS

International Search Report corresponding to European Application No. EP 12 15 0511.9, completed on Apr. 16, 2012 and mailed on Apr. 24, 2012; 7 pages.

International Search Report corresponding to European Application No. EP 12 15 2541.4, completed on Apr. 23, 2012 and mailed on May 3, 2012; 10 pages.

International Search Report corresponding to European Application No. EP 12 16 5609.4, completed on Jul. 5, 2012 and mailed on Jul. 13, 2012; 8 pages.

International Search Report corresponding to European Application No. EP 12 15 8861.0, completed on Jul. 17, 2012 and mailed on Jul. 24, 2012; 9 pages.

International Search Report corresponding to European Application No. EP 12 16 5878.5, completed on Jul. 24, 2012 and mailed on Aug. 6, 2012; 8 pages.

International Search Report corresponding to European Application No. EP 10 25 0715.9, completed on Jun. 30, 2010 and mailed on Jul. 20, 2010; 3 pages.

International Search Report corresponding to European Application No. EP 10 25 0642.5, completed on Mar. 25, 2011 and mailed on Apr. 4, 2011; 4 pages.

International Search Report EP 10 25 0644 dated Jul. 8, 2010.

International Search Report corresponding to European Application No. EP 06 00 4598, completed on Jun. 22, 2006; 2 pages.

International Search Report corresponding to European Application No. EP 06 01 6962.0, completed on Jan. 3, 2007 and mailed on Jan. 11, 2007; 10 pages.

International Search Report corresponding to International Application No. PCT/US05/36740, completed on Feb. 20, 2007 and mailed on Mar. 23, 2007; 8 pages.

International Search Report corresponding to International Application No. PCT/US2008/002981, completed on Jun. 9, 2008 and mailed on Jun. 26, 2008; 2 pages.

International Search Report corresponding to European Application No. EP 08 25 1779, completed on Jul. 14, 2008 and mailed on Jul. 23, 2008; 5 pages.

International Search Report corresponding to European Application No. EP 08 25 1989.3, completed on Mar. 11, 2010 and mailed on Mar. 24, 2010; 3 pages.

International Search Report corresponding to European Application No. EP 05 80 4382.9, completed on Oct. 5, 2010 and mailed on Oct. 12, 2010; 3 pages.

International Search Report corresponding to European Application No. EP 10 25 1437.9, completed on Nov. 22, 2010 and mailed on Dec. 16, 2010; 3 pages.

International Search Report corresponding to European Application No. EP 09 25 2897.5, completed on Feb. 7, 2011 and mailed on Feb. 15, 2011; 3 pages.
International Search Report corresponding to European Application No. EP 11 18 8309.6, completed on Dec. 15, 2011 and mailed on Jan. 12, 2012; 3 pages.
International Search Report from application EP 06016962.0 dated Jan. 3, 2007.
International Search Report from Application PCT/US05/36740 mailed Mar. 23, 2007.
International Search Report from Application No. PCT/US2008/002981 dated Jun. 26, 2008.
International Search Report from Application No. EP 08 25 1779 dated Jul. 23, 2008.

* cited by examiner

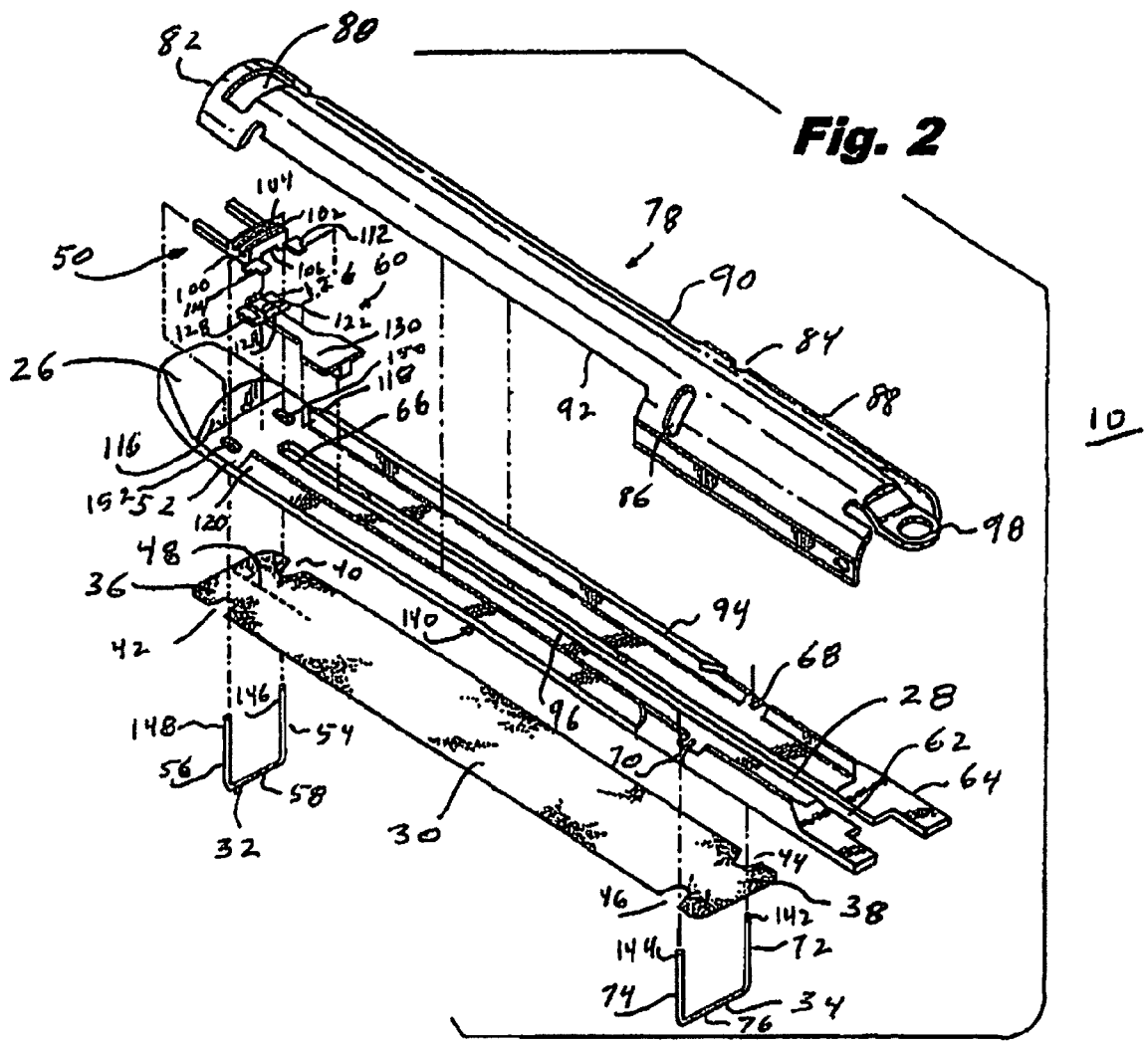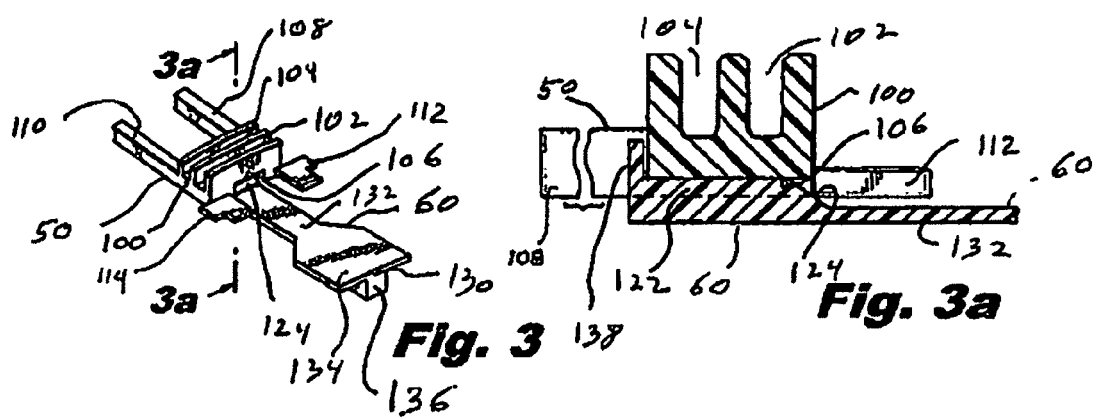

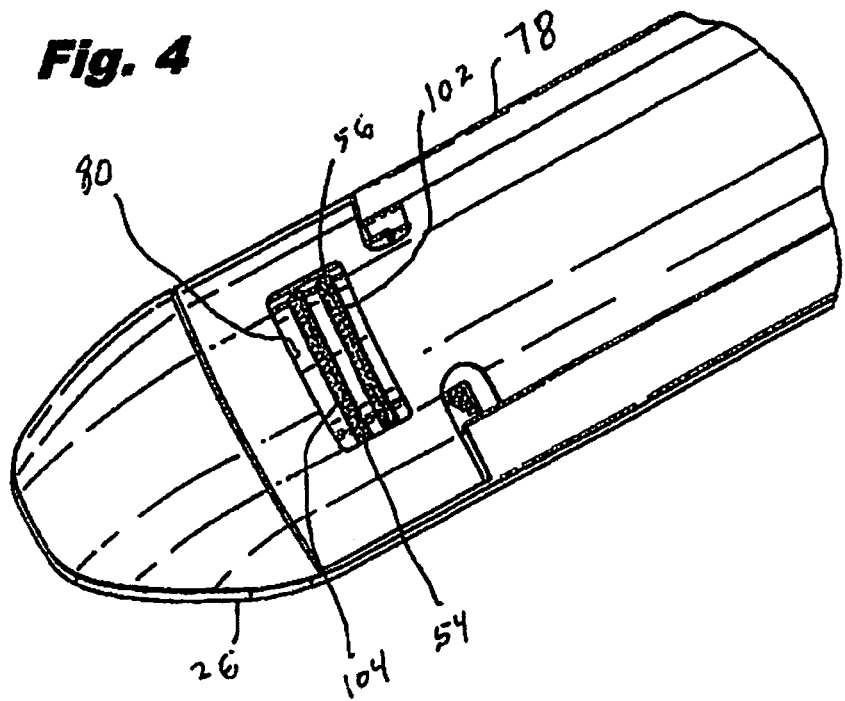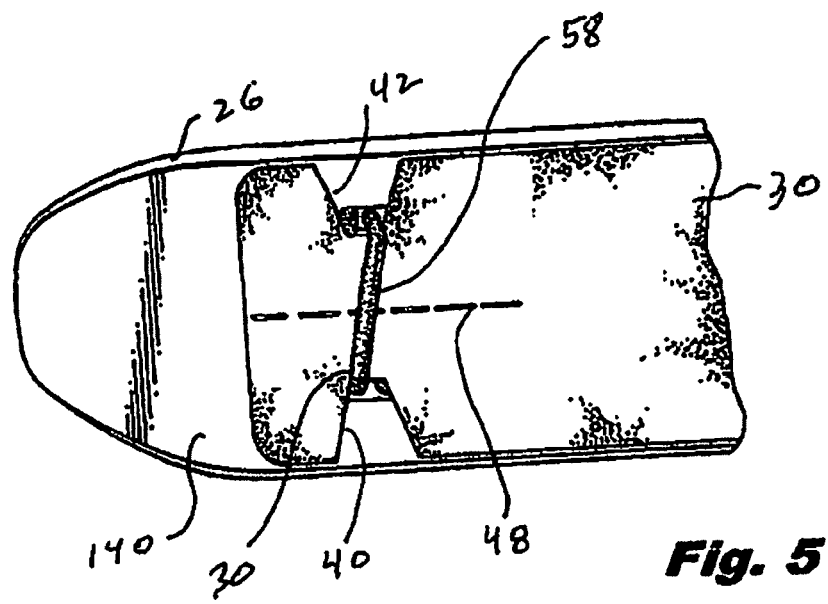

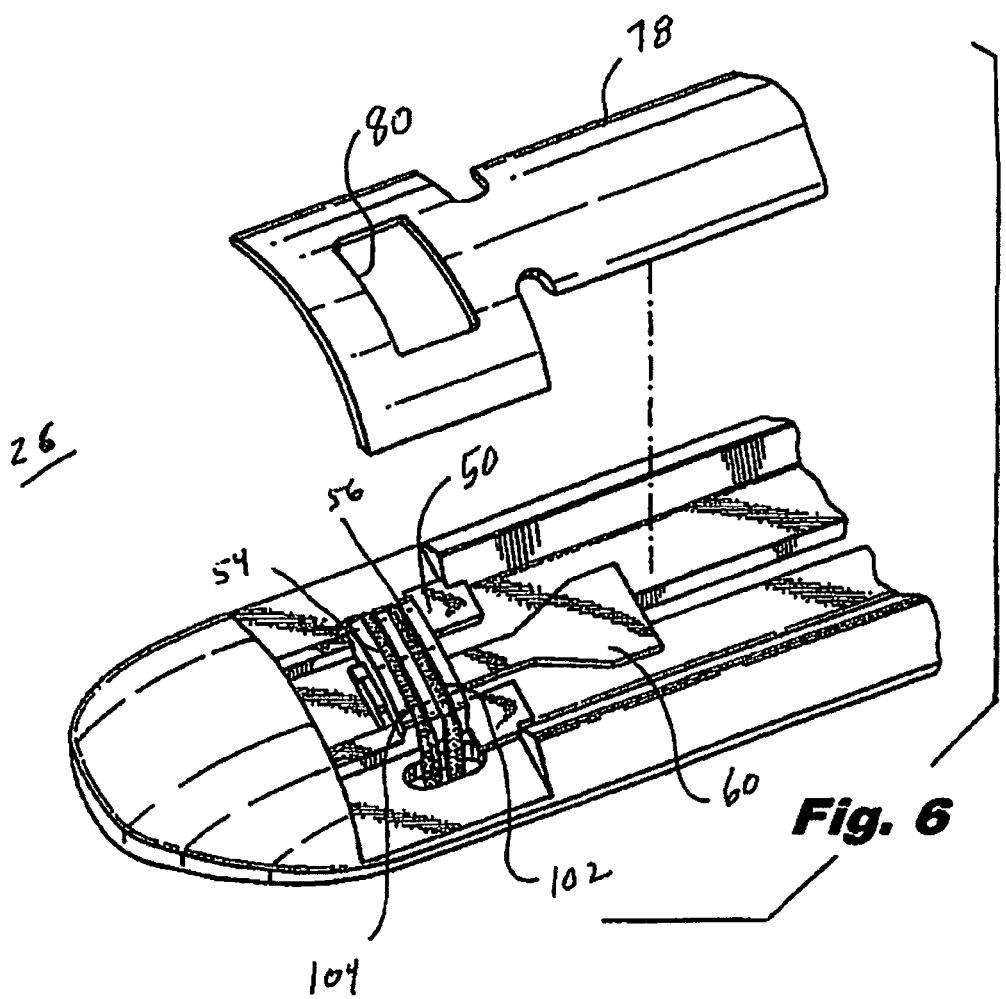
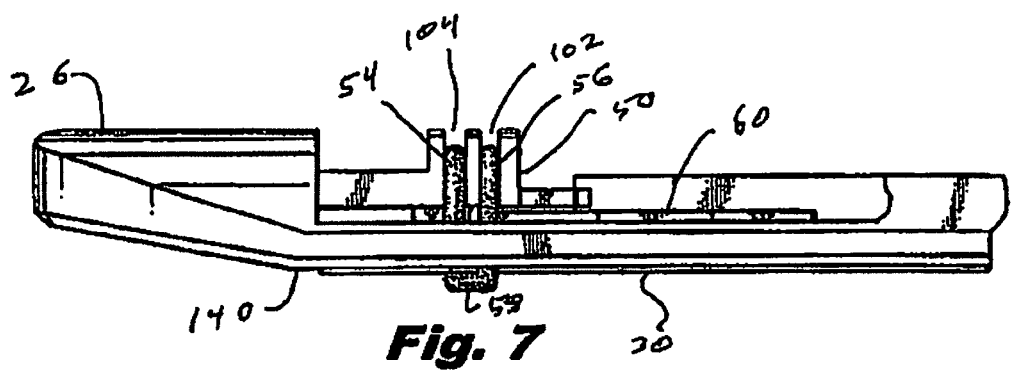

CENTER CINCH AND RELEASE OF BUTTRESS MATERIAL

CROSS-REFERENCE TO RELATED APPLICATIONS

This application is a continuation of U.S. application Ser. No. 13/111,050 filed May 19, 2011, now U.S. Pat. No. 8,235,273, which is a continuation of U.S. application Ser. No. 12/414,961 filed Mar. 31, 2009, now U.S. Pat. No. 7,967,179, and the disclosures of each of the above-identified applications are hereby incorporated by reference in their entirety.

BACKGROUND

1. Technical Field

The present disclosure relates to an anvil assembly incorporating a strip of buttress material for use with a surgical stapling instrument. More particularly, the present disclosure relates to a buttress release mechanism for release of the buttress material from the surgical stapling instrument after stapling.

2. Background of Related Art

During various surgical procedures it is often necessary to join two sides of tissue. This is typically accomplished by approximating two edges of the tissues flush against one another and securing them by stapling, suturing, etc. In some instances, the staple or suture line connecting the tissues may tear or tend to pull through the tissues, particularly, where the tissues are diseased and relatively weak. Additionally, during healing, leakage may occur through the staple or suture lines.

In order to alleviate these problems, a strip of material, called "buttress material" is positioned against the tissues prior to stapling or suturing. The buttress material tends to reinforce the staple or suture line as well as tend to prevent leakage prior to healing.

The buttress material may be attached to the surgical instrument being used. For example, the buttress material is often pre-attached to a staple cartridge or anvil assembly of a surgical stapling instrument. The attachment of the buttress material needs be sufficiently secure to allow the surgical instrument to be inserted into the body of a patient as well as allowing the staple cartridge and anvil to be positioned about specific tissues to be stapled. Furthermore, after stapling of the tissues, the buttress material needs to be attached in a manner which allows easy separation of the buttress material from the associated staple cartridge and/or anvil.

Therefore, it is desirable to provide a cartridge or anvil assembly which is capable of easily releasing the buttress material after tissues have been stapled.

SUMMARY

There is disclosed a buttressed anvil assembly for use with a surgical stapling instrument. The buttressed anvil assembly generally includes an anvil having a strip of buttress material positioned adjacent a bottom side of the anvil. Distal and proximal sutures secure the buttress material to the anvil. A tensioning mechanism is provided at a distal end of the anvil assembly. The tensioning mechanism includes a cinch track engageable with the distal suture to hold a distal end of the strip of buttress material against the anvil. The cinch track is movable between a first vertical position tensioning the distal suture against the strip of buttress material to a second vertical position releasing tension on the distal suture to allow release of the strip of buttress material from the anvil.

A release member is provided in the anvil to move the cinch track between the first vertical position and the second vertical position. The release member includes a wedge engageable within a slot formed in the cinch track. A wedge is movable between a first horizontal position maintaining the cinch track in the first vertical position and a second horizontal position allowing the cinch track to move to the second vertical position. A proximal suture may also be provided to secure a proximal end of the strip of buttress material to a proximal end of the anvil.

Specifically, in a particular embodiment, the anvil assembly generally includes an anvil member having a first side and a second side and a length of suture material passing from the first side of the anvil member to the second side of the anvil member. A cinch track is movably mounted on the first side of the anvil member and is engageable with the length of suture. The cinch track is movable between a first vertical position tensioning the length of suture and a second vertical position releasing tension on the length of suture. A release member is movably mounted on the first side of the anvil member and is movable relative to the cinch track between a first horizontal position and a second horizontal position. The release member maintains the cinch track in the first vertical position when the release member is in the first horizontal position and allows the cinch track to move to the second vertical position when the release member is in the second horizontal position.

The anvil assembly additionally includes a strip of buttress material positioned adjacent the second side of the anvil member. The length of suture includes a backspan and first and second suture sides extending from the backspan. The backspan is engageable with the strip of buttress material to maintain the strip of buttress material adjacent the second side of the anvil member when the cinch track is in the first vertical position.

The anvil member includes first and second holes extending between the first and second sides of the anvil member. The first side of the length of suture material extends through the first hole and the second side of the suture material extends through the second hole. The cinch track includes a first track and the first suture side is secured in the first track. The cinch track also includes a second track and the second suture side is secured in the second track.

The release member includes a wedge and the cinch track includes a slot such that the cinch track is in the first vertical position when the wedge is positioned within the slot and is in the second vertical position when the wedge is out of the slot. The anvil member includes a longitudinally extending slot and the release member includes a guide rib movable within the longitudinally extending slot.

The strip of buttress material includes a perforation line adjacent a distal end of the buttress material to allow separation of the buttress material distally of the anvil slot. The strip of buttress material includes first and second cutouts to accommodate passage of the first and second sides of the length of suture material.

The anvil assembly additionally includes a proximal length of suture material for securing a proximal end of the strip of buttress material to the anvil member. The proximal length of suture material includes a backspan and first and second sides extending from the backspan. The backspan secures a proximal end of the strip of buttress material to the second side of the anvil member. The anvil member includes a pair of slots adjacent the proximal end of the anvil member. The pair of slots is dimensioned to frictionally secure the first and second sides of the proximal length of suture material. The strip of buttress material includes first and second cutouts formed adjacent the proximal end of the strip of buttress material for passage of the first and second sides of the proximal length of suture material.

The anvil assembly further includes a cover affixed to the anvil member. The cover including a distal window providing visualization of the cinch track and a pair of proximal windows providing visualization of the first and second sides of the proximal length of suture material secured within the first and second slots formed in the anvil member.

DESCRIPTION OF THE DRAWINGS

An embodiment of the presently disclosed buttressed anvil assembly is disclosed herein with reference to the drawings, wherein:

FIG. 2 is a perspective view, with parts separated, of the buttressed anvil assembly incorporating a strip of buttress material;

FIG. 3 is a perspective view of a cinch track and release bar of the buttressed anvil assembly;

FIG. 3a is a side view, partially shown in section, taken along the line 3a-3a of FIG. 3;

FIG. 4 is a perspective view of the distal end of the buttressed anvil assembly taken from the top;

FIG. 5 is a perspective view of the distal end of the buttressed anvil assembly taken from the bottom;

FIG. 6 is a perspective view similar to FIG. 4 with an anvil cover removed;

FIG. 7 is a side view of the distal end of the buttressed anvil assembly with the anvil cover removed;

DETAILED DESCRIPTION OF EMBODIMENTS

An embodiment of the presently disclosed buttressed anvil assembly will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
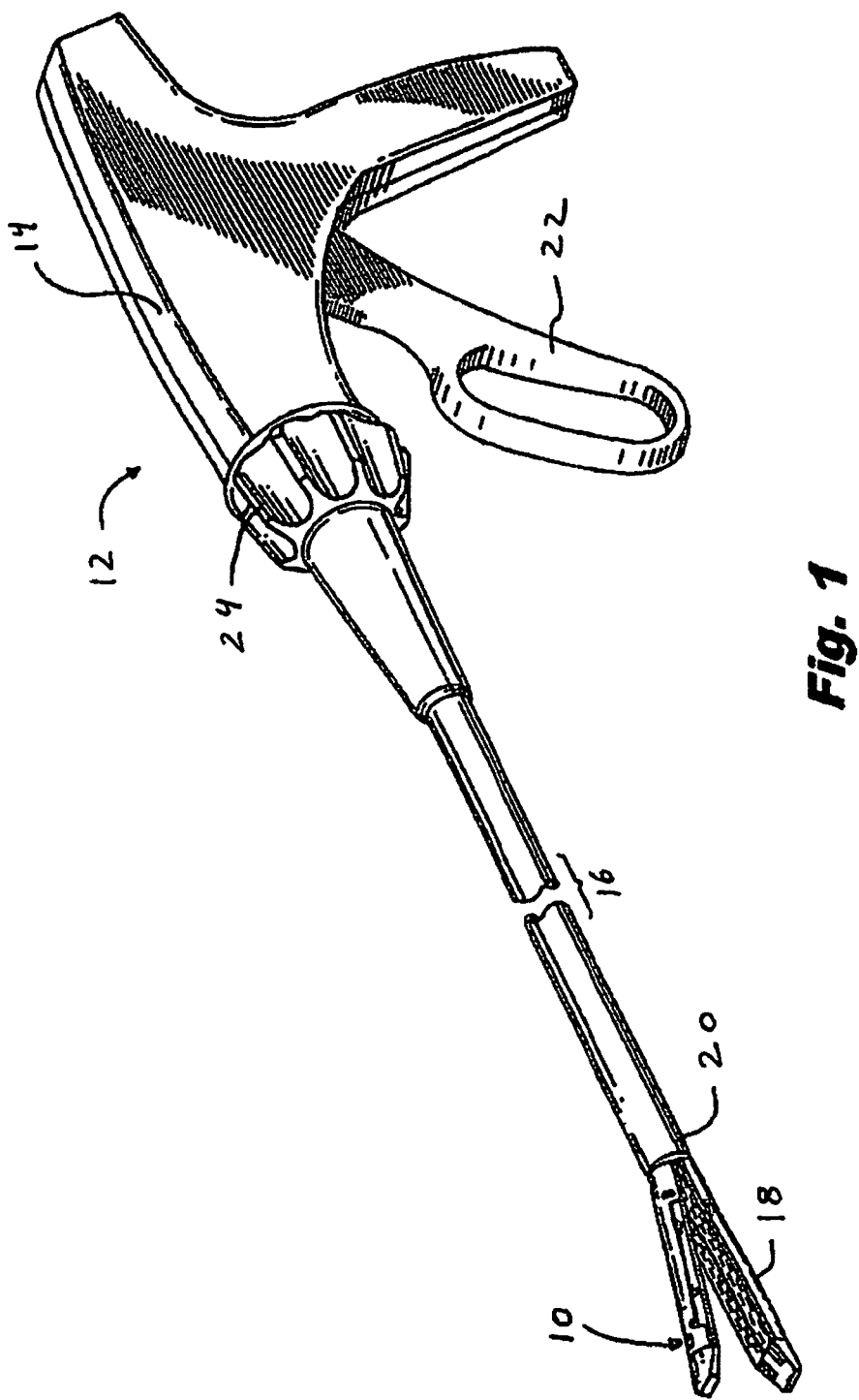
FIG. 1 is a perspective view of a surgical stapling instrument incorporating a buttressed anvil assembly.

Referring to FIG. 1, there is disclosed a buttressed anvil assembly or anvil assembly 10 for use with a surgical stapling instrument 12. As used herein, "buttress" includes pledgets, staple line reinforcement material, gaskets, and other materials used in conjunction with surgical instruments for joining tissue. Surgical stapling instrument 12 is a type well known in the art and is embodied in U.S. Pat. Nos. 5,762,256; 5,782,396; and 6,032,849, the contents of which are expressly incorporated herein by reference.

Surgical stapling instrument 12 generally includes a pistol grip body portion 14 having an elongate tubular member 16 extending distally from body portion 14. A staple cartridge 18 is mounted on a distal end 20 of elongate tubular member 16. Anvil assembly 10 is movably mounted on a distal end 20 of elongate tubular member 16 and is movable between an open position spaced apart from staple cartridge 18 to a closed position wherein anvil assembly 10 is in close cooperative alignment with staple cartridge 18.

In order to move anvil assembly 10 between the open and closed positions, surgical stapling instrument 12 includes a trigger 22 pivotally mounted to body portion 14. Trigger 22 controls the linear movement of an actuation shaft (not shown) which is mounted within the elongated tubular member 16. The actuation shaft operates to move a drive beam (not shown) distally to initially move the anvil assembly 10 between the open and closed positions. The drive beam also acts to move an actuation sled (not shown) distally through the staple cartridge 18 to eject staples. The drive beam includes a knife blade to cut tissue as the drive beam translates through the staple cartridge 18. A rotation knob 24 is provided to orient anvil assembly 10 and staple cartridge 18 relative to the tissue being stapled.

Although surgical stapling instrument 12 is shown with a single trigger 22 which accomplishes both jaw closure and firing of staples, it is further contemplated that the present buttress release mechanism can also be used with surgical stapling instruments of the type which utilize a clamping mechanism to close the jaws which is separate from the firing mechanism. See, for example, U.S. Pat. No. 5,476,206, the contents of which are expressly incorporated herein by reference.

Referring now to FIG. 2, anvil assembly 10 generally includes an anvil member 26, having a knife slot 28 extending longitudinally partially through anvil member 26, and a length or strip of buttress material 30. Strip of buttress material 30 is secured to anvil member 26 by a first or distal suture 32 and a second or proximal suture 34. Distal and proximal sutures 32 and 34 secure respective distal and proximal ends 36 and 38 of buttress material 30 to anvil member 26 in a manner described in more detail hereinbelow.

Buttress material 30 further includes a pair of distal cutouts 40 and 42 formed adjacent distal end 36 of buttress material 30. Distal cutouts 40 and 42 are provided to accommodate passage of distal suture 32 to secure buttress material 30 to anvil member 26 and prevent any distal movement of buttress material 30 relative to anvil member 26. Similarly, a pair of proximal cutouts 44 and 46 is formed adjacent proximal end 38 of buttress material 30. Proximal cutouts 44 and 46 are provided to receive proximal suture 34 to secure proximal end 38 of buttress material 30 to anvil member 26 and prevent any longitudinal motion of buttress material 30. It should be noted that, during stapling and cutting of tissue, distal end 36 of buttress material 30 is distal of knife slot 28 and thus is not cut. A perforation line 48 may be formed in distal end 36 to facilitate separation of buttress material 30 into two halves after tissue has been stapled and cut.

In order to maintain tension of distal suture 32 against buttress material 30 prior to the cutting of tissue and to allow for the release of tension of distal suture 32 against buttress material 30, anvil assembly 10 further includes a cinch track 50 which is positioned within a distal end 52 of anvil member 26. Cinch track 50 is movable between a first vertical position tensioning distal suture 32 against buttress material 30 and a second vertical position releasing tension of distal suture 32 against buttress material 30. Cinch track 50 is provided to securely engage first and second sides 54 and 56 of first suture 32. The suture can be preformed in a shape defining the first side 54, second side 56, and backspan 58, or can comprise an ordinary suture that is wrapped around the anvil so as to defining the first side 54, second side 56, and backspan 58. The backspan 58 of first suture 32 lies against the distal end 36 of buttress material 30 against anvil member 26.

In order to move cinch track 50 between the first and second vertical positions, a release member 60 is provided and is longitudinally or horizontally movable within anvil member 26 in a manner described in more detail hereinbelow. The release member 60 may be formed as a bar, rod, cable or other member.

As shown, knife slot 28 has a proximal end 62 which is open at proximal end 64 of anvil member 26. A distal end 66 of knife slot 28 terminates proximally of distal end 52 of anvil member 26. As noted herein above, buttress material 30 includes a perforation line 48 to facilitate separation of distal end 36 of buttress material 30 as it is located distally of distal end 66 of knife slot 28.

In order to secure a proximal end 38 of buttress material 30 against anvil member 26, anvil member 26 is provided with a pair of slots 68 and 70 which are configured to securely receive first and second sides 72 and 74 of proximal suture 34. The proximal suture can be preformed in a shape or comprise an ordinary suture wrapped around the anvil member so as to define first side 72, second side 74 and backspan 76. The backspan 76 of proximal suture 34 engages proximal end 38 of buttress material 30 to secure proximal end 38 against anvil member 26.

Anvil assembly 10 additionally includes an anvil cover 78 having a distal cinch window 80 formed in a distal end 82 of anvil cover 78. Distal cinch window 80 is provided to allow the surgeon to visually confirm the engagement of distal suture 32 with cinch track 50. A pair of proximal cinch windows 84 and 86 are provided adjacent proximal end 88 of anvil cover 78 and serve to allow the surgeon to visually confirm the engagement of proximal suture 34, specifically the engagement of first and second sides 72 and 74, with slots 68 and 70 formed in proximal end 64 of anvil member 26.

Anvil cover 78 includes longitudinally extending side cuts 90 and 92 which are configured to engage side walls 94 and 96, formed in anvil member 26, in friction fit fashion to secure anvil cover 78 to anvil member 26. Alternatively, the anvil cover may be attached using welding, adhesives or other means. Mounting structure 98 is provided on proximal end 88 to facilitate attachment of anvil assembly 10 to distal end 20 of elongate tubular member 16 (FIG. 1).

The cinch track generally includes a body portion defining one or more tracks. Referring now to FIGS. 3 and 3a, cinch track 50 has a body portion 100 with first and second tracks 102 and 104. First and second tracks 102 and 104 are dimensioned to pinch or cinch first and second sides 54 and 56, respectively, of suture 32 to secure suture 32 to cinch track 50. Body portion 100 additionally includes a center slot 106 for receipt of release member 60 in a matter discussed in more detail hereinbelow.

As noted herein above, cinch track 50 is positioned within distal end 52 of anvil member 26 and is movable between first and second vertical positions relative to anvil member 26. As specifically shown in FIG. 3, a pair of distal arms 108 and 110 extend distally from body portion 100 while proximal tabs 112 and 114 extend proximally from body portion 100. Distal arms 108 and 110 are positioned against a proximal face 116 formed in distal end 52 of anvil member 26 (FIG. 2). Likewise, proximal tab 112 and proximal tab 114 are configured to loosely engage distal ends 118 and 120 of side walls 94 and 96 formed in anvil member 26 allowing cinch track 50 to move vertically within distal end 52 of anvil member 26 (FIG. 2).

Referring back for the moment to FIG. 2, as noted herein above, release member 60 is provided to move cinch track 50 between the first and second vertical positions. Release member 60 includes a distal wedge 122 which is configured to ride within center slot 106 of cinch track 50 to move cinch track 50 between the first and second vertical positions. A sloped face 124 extends proximally from distal wedge 122. Sides 126 and 128 of distal wedge 122 facilitate guiding distal wedge 122 against cinch track 50. In the embodiment of FIG. 3a, the bottom surface of the cinch track 50 is generally horizontal. However, in other embodiments, one or more surfaces can be shaped to cooperate with the sloped face 124, such as a cam surface, and may correspond to the shape of the sloped face 124.

Referring now to FIG. 3, release member 60 further includes a guide bar 130 extending proximally from distal wedge 122. Guide bar 130 includes a central portion 132 and a proximally extending flanged portion 134. Flanged portion 134 helps align release bar 60 within side walls 94 and 96 of anvil member 26. As shown, a guide rib 136 extends downwardly from guide bar 130 and is configured to ride within knife slot 28 such that release member 60 is movable in a longitudinal or horizontal direction relative to cinch track 50.

With specific reference to FIG. 3a, it can be seen that wedge 122 of release member 60 is configured to move body portion 100 of cinch track 50 vertically. Sloped face 124 of release member 60 facilitates assembly of anvil assembly 10, and specifically, allows for reset of release member 60 to pre-fire and assembly condition. A base stop 138 is provided on distal wedge 122 of release member 62 to prevent pulling wedge 122 completely through center slot 106 of cinch track 50 during assembly.

Referring now to FIGS. 2-7, and initially with regard to FIG. 2, the assembly of a strip of buttress material 30 to anvil member 26 will now be described. Proximal end 38 of strip of buttress material 30 is secured to proximal end 64 of anvil member 26. Specifically, proximal end 38 is positioned against an underside 140 of anvil member 26. Proximal suture 34 is manipulated such that first and second free ends 142 and 144 of first and second sides 72 and 74 pass through cutouts 44 and 46 to bring backspan 76 of proximal suture 34 into engagement with proximal end 38 of strip of buttress material 30.

Thereafter, first and second sides 72 and 74 are positioned within slots 68 and 70 in anvil member 26. During positioning, first and second side 72 and 74 are tensioned so as to secure proximal end 38 of strip of suture material 30 against underside 140 of anvil member 26. As noted herein above, slots 68 and 70 are dimensioned so as to pinch or cinch first and second sides 72 and 74. Once strip of suture material 30 has been secured, the excess material of first and second side 72 and 74 extending beyond slots 68 and 70 may be trimmed off through the cover. It should be noted that, since proximal end 38 of strip of suture material 30 stretches across knife slot 28, there is no need to release the tension on proximal suture 34 as it will be cut by a knife blade (not shown) during the stapling procedure.

With reference to FIGS. 2-7, the assembly of distal end 36 of strip of suture material 30 to anvil member 26 will now be described. Initially, with respect to FIGS. 3 and 3a, release member 60 is in a first or proximal most position. Cinch track 50 is in a first or vertically highest most position due to the passage and engagement of wedge 122 of release member 60 within slot 106 formed in body portion 100 of cinch track 50.

With reference to FIG. 2, distal end 36 of strip of buttress material 30 is positioned flush against underside 140 of anvil member 26. Distal suture 32 is manipulated such that free ends 146 and 148 of first and second sides 54 and 56, respectively, passed through cutouts 40 and 42 formed in distal end 36 of strip of buttress material 30. As shown, distal end 52 of anvil member 26 is provided with a pair of spaced apart holes 150 and 152. Free ends 146 and 148 of distal suture 32 are passed through holes 150 and 152 such that first and second sides 54 and 56 are aligned alongside first and second tracks 102 and 104 of cinch track 50. Vertical tension is applied to free ends 146 and 148 to secure distal end 36 of strip a buttress material 30 against underside 140 of anvil member 26.

First and second sides 54 and 56 are then manipulated such that first side 54 passes within second track 104 and second side 56 passes within first track 102 (see also FIGS. 6 and 7). As noted herein above, first and second tracks 102 and 104 are dimensioned so as to pinch or cinch a suture positioned therein. Thereafter, excess material of first and second sides 54 and 56 of distal suture 32 may be trimmed off. Finally, cover 78 is affixed to anvil member 26 in the manner described herein above.

With reference to FIGS. 4 and 5, in the assembled condition, first and second sides 54 and 56 of distal suture 32 are visible through distal cinch window 80 in cover 78 for verification (FIG. 4). Likewise, backspan 58 of distal suture 32 can be confirmed as extending across perforation line 48 and strip of suture material 30 (FIG. 5).

Referring now to FIGS. 1 and 6-10, the use of anvil assembly 10 will now be described. With reference to FIGS. 6 and 7, and as described herein above, in the initial position release bar 60 is in a first or proximal most position maintaining cinch track 50 in a first or vertically highest position relative to anvil member 26 thereby maintaining tension of backspan 58 of distal suture 32 against distal end 36 of strip of buttress material 30.

In use, with reference to FIG. 1, surgical stapling instrument 12 is manipulated such that anvil assembly 10 and staple cartridge 18 are positioned about the tissue (not shown) to be stapled. Once surgical stapling 12 has been properly positioned, trigger 22 is actuated to move anvil assembly 10 to the closed position about tissue relative to staple cartridge 18. While not specifically shown, anvil pockets are provided on anvil member 26 to clinch staples ejected out of staple cartridge 18 through the subject tissue and through strip of buttress material 30.

Figure 8:
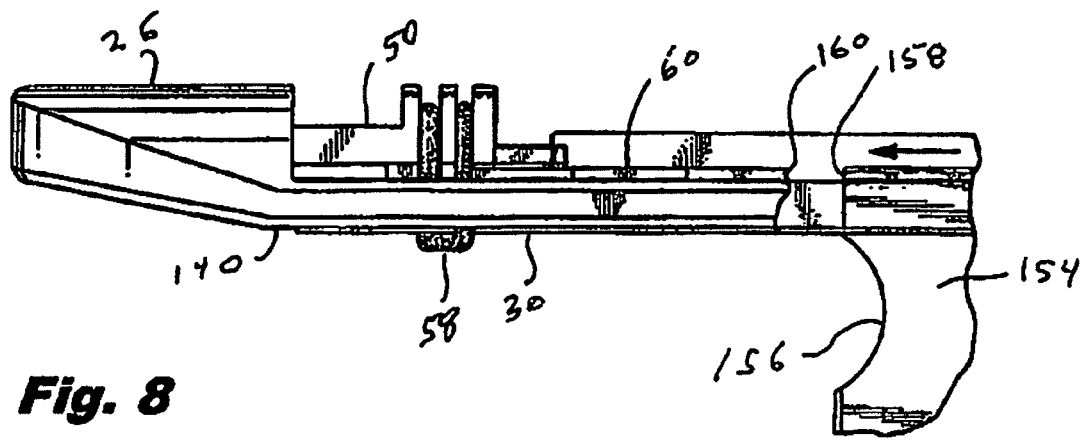
FIG. 8 is a side view similar to FIG. 7 during the initial advancement of a knife bar toward the release bar.

Referring back for the moment to FIG. 2, and as noted herein above, backspan 76 of proximal suture 34 extends across knife slot 28. Referring now to FIG. 8, a knife bar 154 is associated with surgical stapling instrument 12 to cut through staple lines formed in the tissue by staple cartridge 18 and anvil assembly 10. As knife bar 154 passes distally through knife slot 28 a blade 156 of knife bar 154 cuts through proximal end 38 of strip of buttress material 30 and severs backspan 76 a proximal suture 34. Continued advancement of knife bar 154 distally through slot 28, causes blade 156 to continue to cut through strip of buttress material 30.

Figure 9:
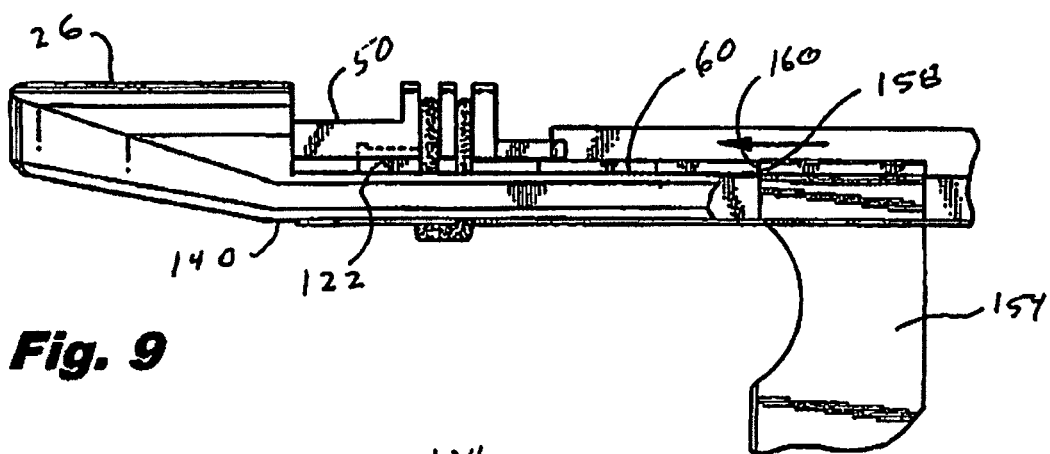
FIG. 9 is a side view similar to FIG. 8 illustrating the engagement of the knife bar with the release bar.

With continued reference to FIG. 8, as knife bar 154 advances distally through anvil member 26, a distal top edge 158 of knife bar 154 approaches a proximal edge 160 of release member 60. As best shown in FIG. 9, as distal edge 158 of knife bar 154 moves distally it engages proximal edge 160 of release member 60, knife bar 154 begins to drive release member 60 distally such that distal wedge 122 of release member 60 is driven distally through slot 106 (FIGS. 2 and 3) formed in cinch track 50.

Figure 10:
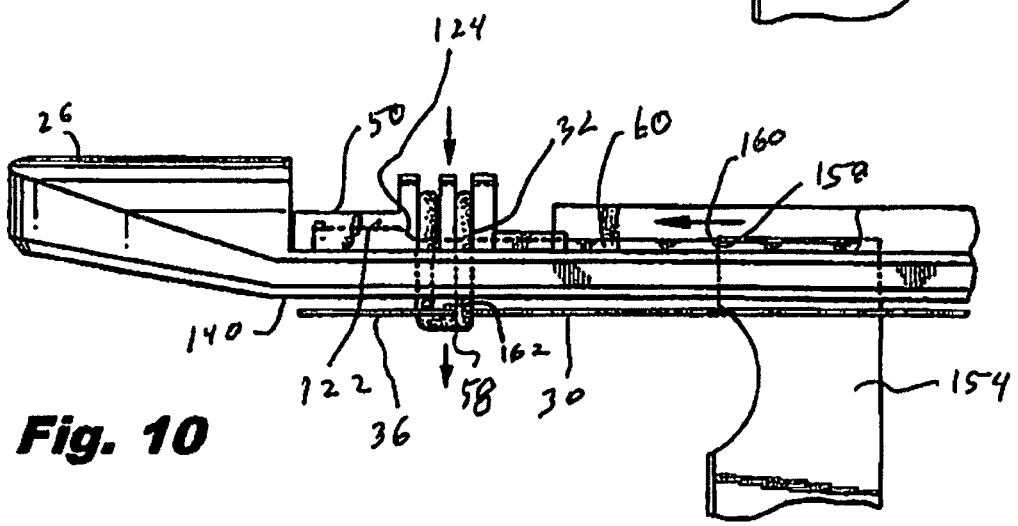
FIG. 10 is a side view similar to FIG. 8 illustrating the knife bar advancing the release bar through the cinch track to release tension on the strip of buttress material.

With specific reference to FIG. 10, as release member 60 is driven to a second or distal most position by a knife bar 54, sloped face 124 of distal wedge 122 clears slot 106 allowing cinch track 50 to drop down to a second or vertically lowest most position relative to anvil member 26. As shown, when cinch track 50 is in the second or vertically lowest position, tension is released on distal suture 32 such that backspan 58 of distal suture 32 drops a substantial distance below underside 140 of anvil member 26. This creates an opening or gap 162 between backspan 58 of distal suture 32 and underside 140 of anvil member 26.

Once knife bar 154 has reached a distal most position, pressure on trigger 22 may be released allowing anvil member 10 to move to the open position relative to staple cartridge 18 (FIG. 1). As anvil assembly 10 is moved to the open position, distal end 36 of strip of buttress material 30, being stapled the tissue, pulls free through gap 162 allowing distal end 36 to separate from anvil member 26. As noted herein above, and as shown in FIG. 2, perforation line 48 is formed in distal end 36 of strip of buttress material 30 allowing strip of buttress material 30 to separate into halves generally along the cut line formed by knife blade 156 through strip of buttress material 30. In this manner, anvil assembly 10 allows for simple and easy assembly of a strip of buttress material 30 to with anvil member 26 and, more importantly, allows for easy release of distal end 36 of a strip of buttress material 30 from anvil member 26.

It will be understood that various modifications may be made to the embodiments disclosed herein. For example, the release member could be arranged to be pulled proximally to change the position of the cinch track and release the suture and buttress. In other embodiments, the proximally pulled release member, or the release member 60 discussed above, may be connected to a separate actuator on the handle of the surgical instrument, for engagement by the user of the instrument. In another example, the disclosed cinch track may have more or fewer tracks to accommodate more or fewer wraps of a length of suture material. Further, the disclosed tensioning mechanisms, including the suture track and the release bar, may be adapted to be incorporated in a staple cartridge and to function with driving bars in the staple cartridge. Additionally, the disclosed methods and structure for releasing tension on a suture maintaining a strip of buttress material may find use in other forms of surgical staplers such as, for example, circular staplers, etc. In further embodiments, a release member pushes cinch track down vertically to release the tension on the suture and release the buttress. Therefore, the above description should not be construed as limiting, but merely as exemplifications of particular embodiments. Those skilled in the art will envision other modifications within the scope and spirit of the claims appended hereto.

The invention claimed is:

1. A cartridge assembly comprising:
   a staple cartridge having a plurality of staples and a tissue contacting surface;
   a strip of buttress material secured to the staple cartridge with a suture member extending across the tissue contacting surface of the staple cartridge;
   a tensioning member engaging the suture member, the tensioning member being movable between a first position tensioning the suture member and a second position releasing tension on the suture member.

2. The cartridge assembly as recited in claim 1, wherein the suture member includes first and second suture sides.

3. The cartridge assembly as recited in claim 2, wherein the tensioning member includes a first track and the first suture side is secured in the first track.

4. The cartridge assembly as recited in claim 3, wherein the tensioning member includes a second track and a second suture side is secured in the second track.

5. The cartridge assembly as recited in claim 2, further comprising a release member that is movable to interact with the tensioning member to move the tensioning member to the second position.

6. The cartridge assembly as recited in claim 5, wherein the release member includes a wedge for maintaining the tensioning member in the first position.

7. The cartridge assembly as recited in claim 2, wherein the staple cartridge includes first and second holes, the first side of the suture member extending through the first hole and the second side of the suture member extending through the second hole.

8. The cartridge assembly as recited in claim 1, wherein the strip of buttress material includes a perforation to facilitate separation of the strip of buttress material.

9. The cartridge assembly as recited in claim 1, wherein the suture member is disposed at a distal end of the staple cartridge, and a further suture member is disposed at a proximal end of the staple cartridge.

10. A surgical stapling apparatus, comprising:
a pair of jaws, one of the jaws including a staple cartridge and the other of the jaws being an anvil assembly, each of the pair of jaws having a tissue contacting surface;
a suture member passing across the tissue contacting surface of at least one of the pair of jaws; and
a tensioning member movably mounted on a first side of the anvil assembly and engageable with the suture member, the tensioning member movable between a first position tensioning the suture member and a second position releasing tension on the suture member.

11. The surgical stapling apparatus as recited in claim 10, further comprising a strip of buttress material positioned adjacent the tissue contacting surface of the at least one of the pair of jaws.

12. The surgical stapling apparatus as recited in claim 10, further comprising a knife assembly including a knife blade.

13. The surgical stapling apparatus as recited in claim 12, wherein the anvil assembly includes an anvil member.

14. The surgical stapling apparatus as recited in claim 13, wherein the anvil member includes a knife slot, wherein the knife blade is distally movable through the knife slot.

15. The surgical stapling apparatus as recited in claim 10, wherein the suture member is disposed at a distal end of the staple cartridge, and a further suture member is disposed at a proximal end of the staple cartridge.

16. The surgical stapling apparatus as recited in claim 10, further comprising a release member movably mounted to engage the tensioning member to move the tensioning member to the second position.

* * * * *